United States Patent
Aihara et al.

[11] Patent Number: 5,891,359
[45] Date of Patent: Apr. 6, 1999

[54] LIQUID CRYSTAL COMPOUND

[75] Inventors: Yoshihiko Aihara; Tadaaki Isozaki; Noriko Yamakawa; Ichiro Kawamura, all of Tokyo, Japan

[73] Assignee: Showa Shell Sekiyu Kabushiki Kaisha, Tokyo, Japan

[21] Appl. No.: 899,361

[22] Filed: Jun. 16, 1992

Related U.S. Application Data

[63] Continuation-in-part of Ser. No. 863,316, Apr. 1, 1992, abandoned, which is a continuation of Ser. No. 736,596, Jul. 26, 1991, abandoned.

[30] Foreign Application Priority Data

Jul. 30, 1990 [JP] Japan ................................ 2-201607

[51] Int. Cl.$^6$ ........................... C09K 19/32; C07C 69/76
[52] U.S. Cl. ...................... 252/299.62; 560/100
[58] Field of Search ....................... 252/299.62; 560/100

[56] References Cited

U.S. PATENT DOCUMENTS 4,973,738  11/1990  Suzuki et al. ............................ 560/80
5,075,032  12/1991  Hopf et al. .

FOREIGN PATENT DOCUMENTS 0341922  11/1989  European Pat. Off. .

*Primary Examiner*—C. H. Kelly
*Attorney, Agent, or Firm*—Pillsbury Madison & Sutro LLP

[57] ABSTRACT

The novel liquid crystal compounds of the present invention are represented by the following formulas [I]–[II] and have tristable molecular orientation states and can be used for display devices and electrooptical devices.

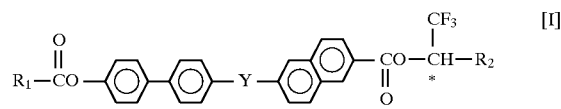

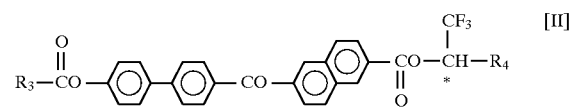

wherein $R_1$ represents an alkyl group of 5–18 carbon atoms; $R_2$ represents an alkyl group of 6–16 carbon atoms; $R_3$ represents an alkyl group of 8–18 carbon atoms; $R_4$ represents an alkyl group of 6–14 carbon atoms; Y represents

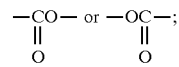

and * indicates an optically active center.

8 Claims, 9 Drawing Sheets

LIQUID CRYSTAL COMPOUND

This is a continuation-in-part of the FWC 62 Continuation application Ser. No. 07/863,316 filed Apr. 1, 1992, now abandoned, which is a Continuation application Ser. No. 07/736,596 filed Jul. 26, 1991, now abandoned.

The present invention relates to ferroelectric chiral smectic liquid crystal compounds which are used for display devices or electrooptical devices utilizing responses to electric fields.

Furthermore, the present invention relates to antiferroelectric liquid crystal compounds which show three stable molecular orientations, and optically tristable states. The liquid crystal compounds are used for display devices or electrooptical devices utilizing response to electric fields.

As electrooptical displays utilizing nematic liquid crystals such as DSM type, TN type, G-H type, and STN type have been developed and practically used. However, their use is restricted because of their slow response time as slow as a few millisec to some ten millisec. The slow response speed of devices which use nematic liquid crystals is due to the fact that torque for moving molecules is not so large since the torque is based on anisotropy of dielectric constant. Under such circumstances, Meyer et al. developed ferroelectric liquid crystals which have large spontaneous polarization (Ps), and have a large torque (Ps×E, where E is an applied electric field). Thus they have a high response speed of a few psec to some ten $\mu$sec. (Meyer et al, Le Journal de Physique, 36, 1975, L-69). Another novel antiferroelectric liquid crystal is disclosed in Japanese Patent Kokai No. 63-307837. The term "tristable states" referred to hereinafter is disclosed in Japanese Patent Kokai Nos. 1-316367, 1-316372, 1-316339, 2-28128, 2-131450, 2-160748 and No. 1-213390.

Some high speed electrooptical devices utilizing ferroelectric liquid crystals have been proposed.

A typical example is a device where a helical structure is released by wall forces and change is brought about in two molecular orientations which become parallel to the wall by polarity of applied fields (Japanese Patent Kokai No. 56-107216).

The above one is based on a premise that there is a compound having an ideal bistable states as shown in response wave to electric field of FIG. 1. However, such compound which has the ideal bistable states has not yet been found. Response wave to electric field of bistable state liquid crystals which have been actually synthesized is as shown in FIG. 2 and the response wave as shown in FIG. 1 has not been obtained. When such liquid crystal having the response wave as shown in FIG. 2 is used, for example, for switching circuits for light, the object cannot be sufficiently attained by only a change in applied electric voltage between "ON" and "OFF", since percent transmittance gradually changes as applied electric voltage changes from $\ominus$ side to $\oplus$ side. Moreover, it is difficult for the bistable-state liquid crystals which have been hitherto synthesized to form a monodomain structure which is an ideal molecular orientation at an S*c phase stage where no electric field is applied to and disclination (defect) is formed or a disturbance called twist is caused in molecular orientation. Thus, it is difficult to realize the ideal bistable-state orientation with large area. Furthermore, since threshold value (voltage at which luminance varies by a given value) is small, contrast decreases or field of view narrows when dynamic driving is applied. Besides, the bistable-state liquid crystals which have been actually synthesized cannot show the hysteresis as shown in FIG. 1, but shows the hysteresis as shown in FIG. 2 and so they have no memory effect. Therefore, a large amount of energy is lost in order that the liquid crystals retain a stable response at the S*c phase, since the voltage $v_3$ in FIG. 2 or a high frequency must be continuously applied.

Although high speed liquid crystal electrooptical devices which utilize effectively the strong bonding between applied electric field and molecular orientation of ferroelectric liquid crystals are desired, there are still many problems to be solved.

Therefore, the object of the present invention is to provide novel liquid crystal compounds which can be used for liquid crystal electro-optical devices utilizing the tristable states to make high speed response possible where stable molecular orientations of clear contrast are realized depending on electric fields applied, clear threshold specificity and clear hysteresis as shown in FIG. 3 are revealed, and dynamic driving can easily be realized.

In the present invention, novel antiferroelectric liquid crystals are provided which have novel tristable states different from chiral smectic S phase (S*c phase) which is a conventional bistable-state phase.

The term "having tristable states" means that an electrooptical device where antiferroelectric liquid crystals are laid between the first electrode substrate plate and the second electrode substrate plate which is apart at a given space from the first one is constructed. A triangular wave voltage is applied to both the first and second electrode substrate plates as shown in FIG. 4A. The antiferroelectric liquid crystals have molecular orientation of the first stable state (as shown in FIG. 4D-2) where no electric field is applied, but upon application of electric field, molecular orientation of the second stable state (as shown in FIG. 4D-1) which is different from the first stable state in one of electric field directions and molecular orientation of the third stable state (as shown in FIG. 4D-3) which is different from the first and second stable states in the other direction of electric field. Liquid crystal electrooptical devices utilizing this tristable states are disclosed in Japanese Patent Kokai No. 2-153322.

On the other hand, "commercially available nematic liquid crystals" or bistable state liquid crystals do not have the three stable states as shown in FIG. 4B and C.

The novel tristable state antiferroelectric liquid crystals exhibit epoch-making effects when they are used in liquid crystal devices as compared with conventional nematic liquid crystals.

For obtaining high image quality, the conventional liquid crystals require much complicated structure driven by active matrix system while the tristable state antiferroelectric liquid crystals require simple matrix displays. Therefore, the high production cost and complicated fabrication processes of the conventional liquid crystal device restrict their scope for large scale production, while for the tristable state antiferroelectric liquid crystals, production processes are simple even for large scale displays. As the result the production cost is relatively low.

BRIEF DESCRIPTION OF DRAWINGS

In FIGS. 1–3, abscissa axis shows applied voltage and ordinate axis shows transmittance (%).

FIG. 9A–9E show triangular wave voltage applied to liquid crystal cells and hysteresis curves when the triangular wave voltage is applied to.

Figure 1:
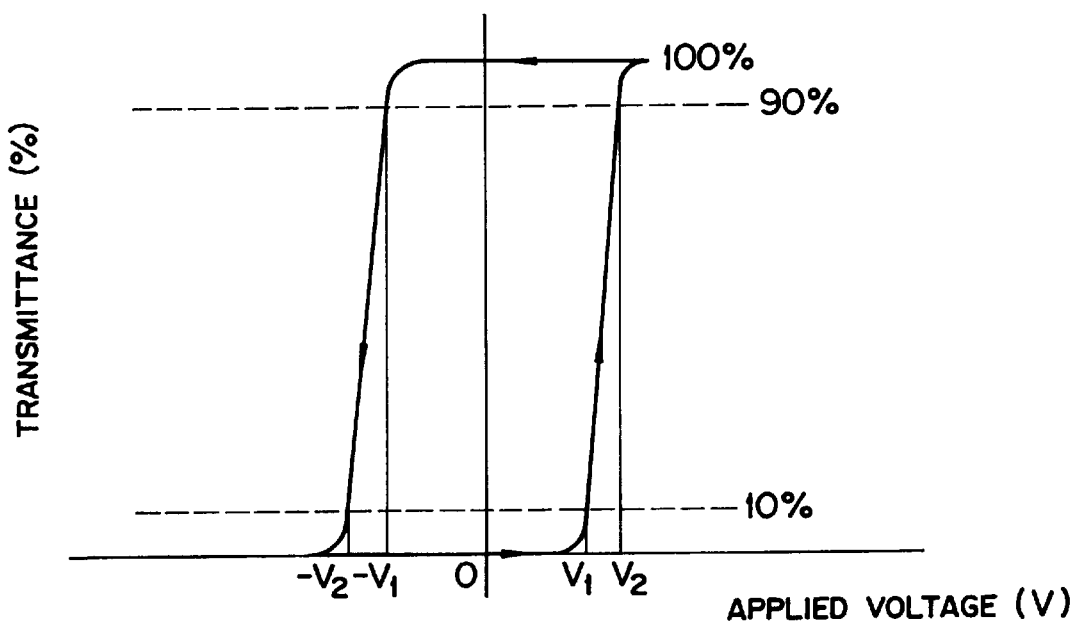
FIG. 1 shows hysteresis of ideal bistable-state liquid crystal which has not been actually obtained.
Figure 2:
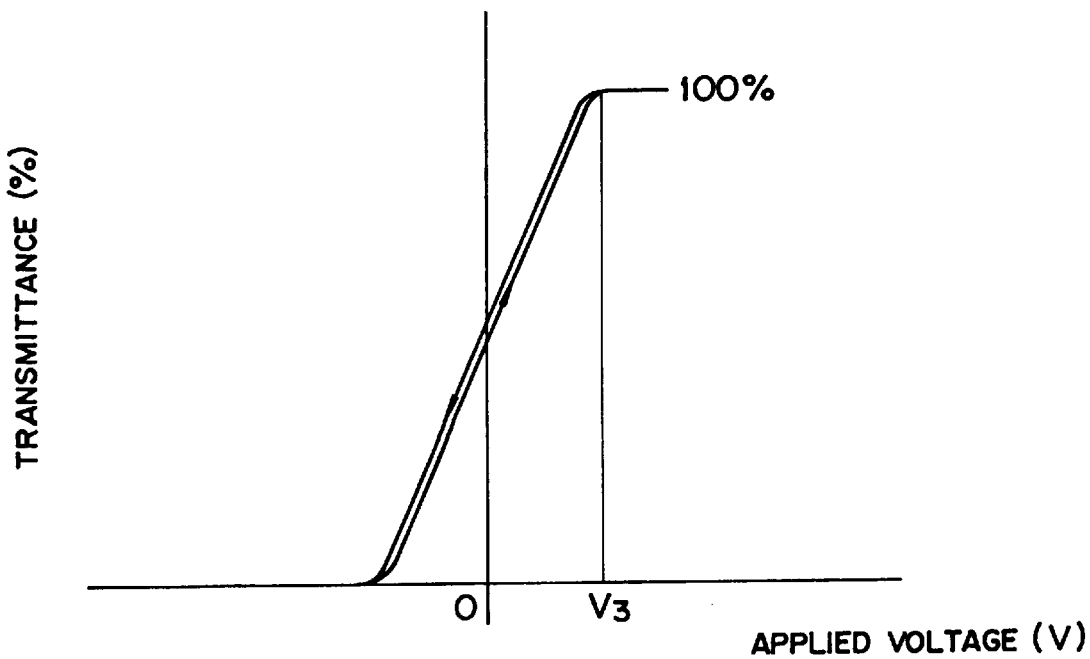
FIG. 2 shows hysteresis of bistable-state liquid crystal which has been actually synthesized.
Figure 3:
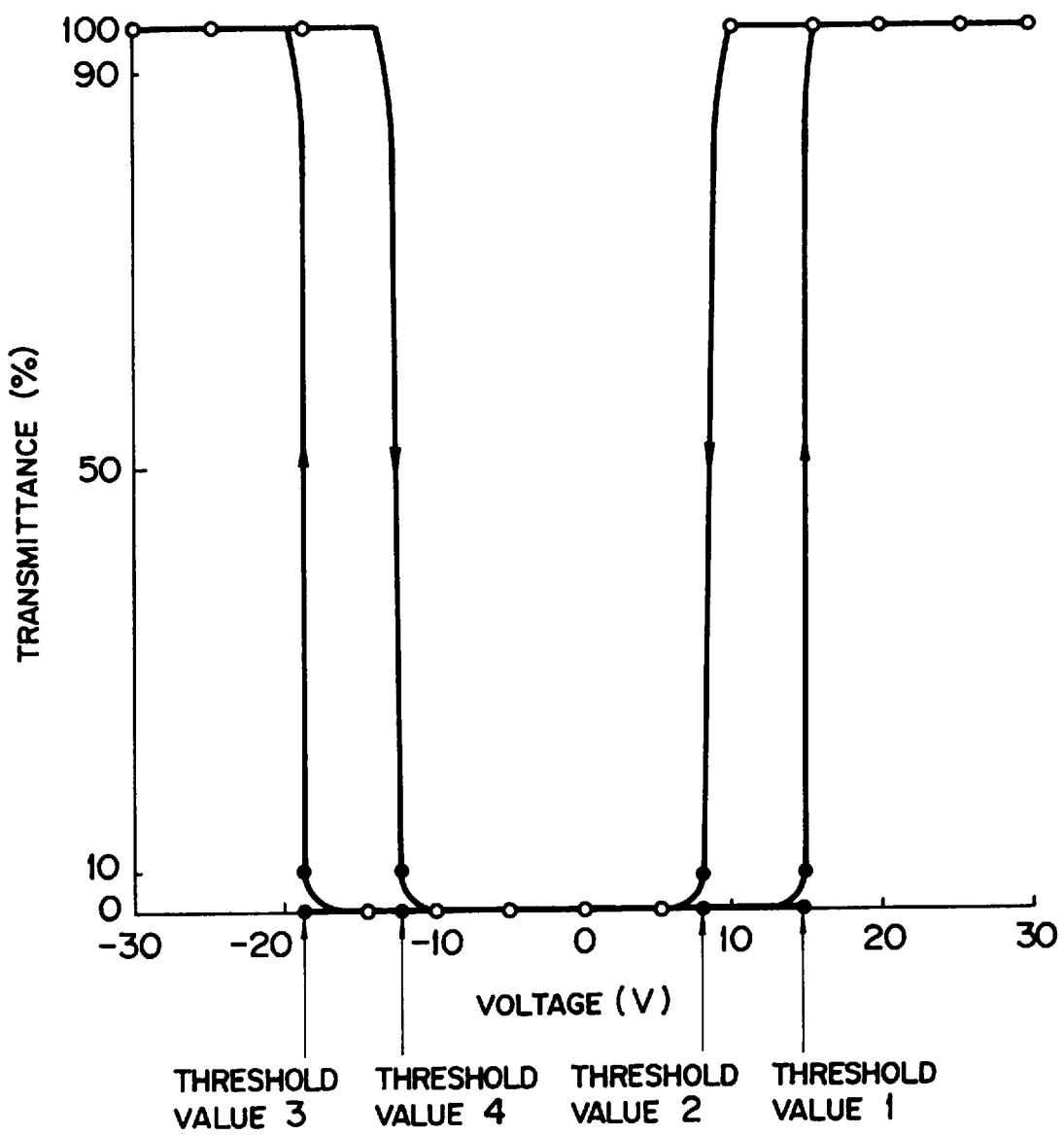
FIG. 3 shows hysteresis of the tristable-state liquid crystal of the present invention.
Figure 4:
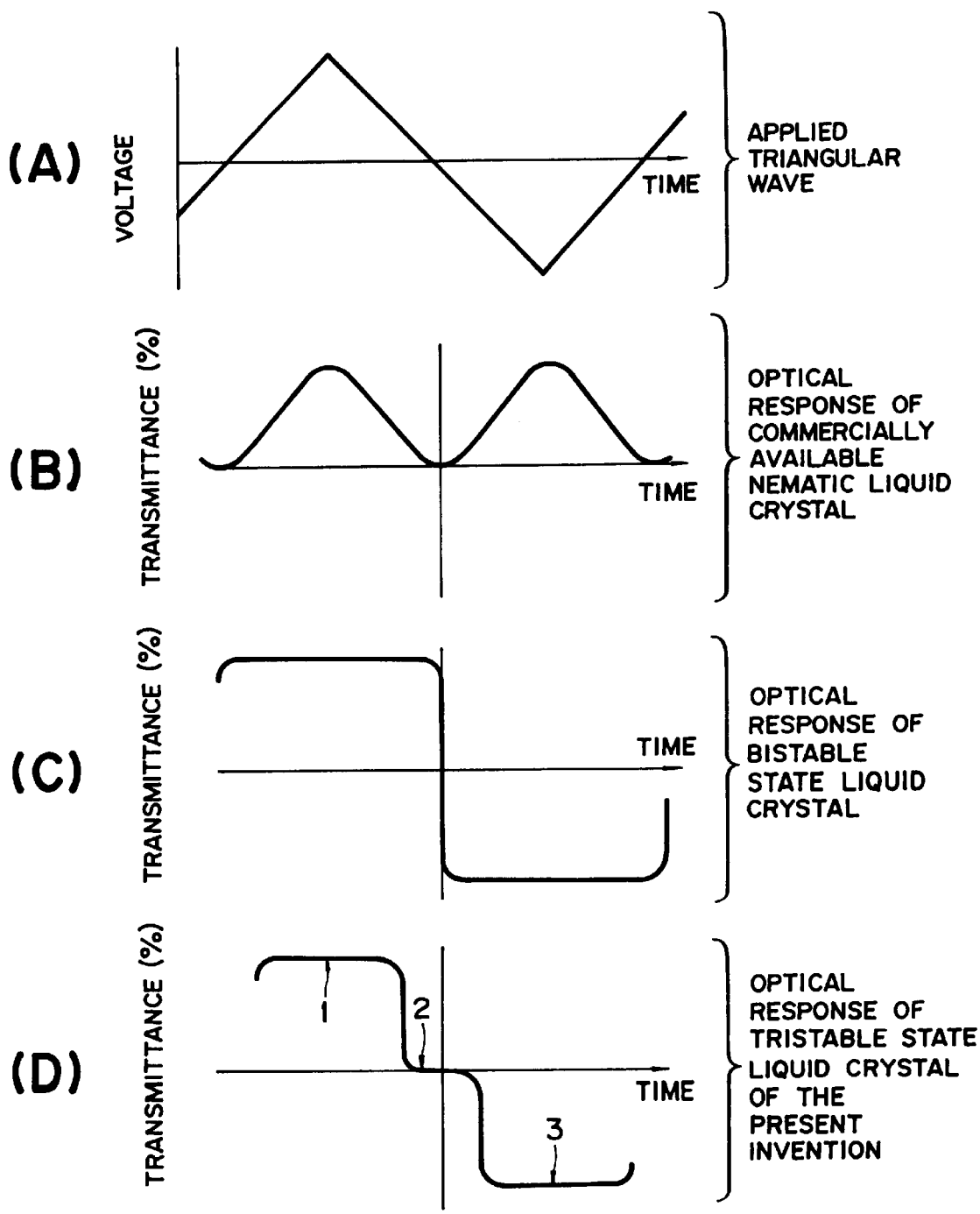
FIG. 4A shows applied triangular wave.
FIGS. 4B, 4C and 4D show optical response of commercially available nematic liquid crystal, that of bistable state liquid crystal, and that of tristable-state liquid crystal, respectively.

The first of the present invention relates to a liquid crystal compound having a naphthalene nucleus which is represented by the formula (I):

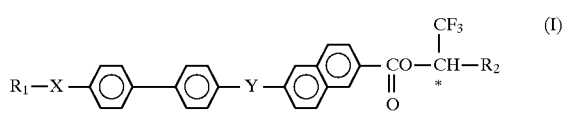

wherein $R_1$ represents an alkyl group of 5–18 carbon atoms; $R_2$ represents an alkyl group of 6–16 carbon atoms; X represents a —O—,

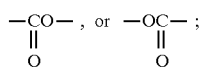

Y represents

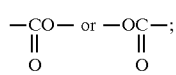

and * indicates an optically active center.

The second of the present invention relates to a liquid crystal compound having optically tristable states which is represented by the formula (II):

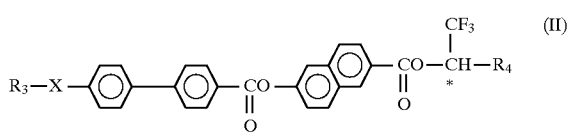

wherein $R_3$ represents an alkyl group of 6–18 carbon atoms; $R_4$ represents an alkyl group of 6–14 carbon atoms; X represents a —O—,

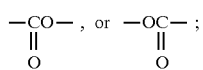

and * indicates an optically active center.

The third of the present invention relates to a liquid crystal compound having optically tristable states which is represented by the formula (III):

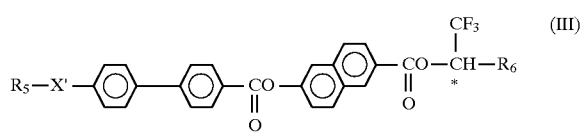

wherein $R_5$ represents an alkyl group of 6–18 carbon atoms; $R_6$ represents an alkyl group of 6–14 carbon atoms; X' represents

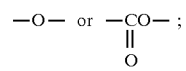

and * indicates an optically active center.

The liquid crystal compounds of the present invention can be used for liquid crystal electrooptical devices utilizing optically tristable states and besides, can be used for liquid crystal electrooptical devices utilizing conventional optically bistable-stable liquid crystals.

Some synthesis examples of the present compounds are shown below.

(A)

(i) 2-Hydroxy-6-carboxynaphthalene is allowed to react with an optically active 1,1,1-trifluoro-2-alkanol in ethylene chloride in the presence of sulfuric acid to obtain 1,1,1-trifluoro-2-alkyl 6-hydroxynaphthalene-2-carboxylate.

(ii) The reaction product is allowed to react with 4-n-alkyloxybiphenyl-4'-carboxylic acid in the presence of dicyclohexylcarbodiimide to obtain 1,1,1-trifluoro-2-alkyl 6-[4-(n-alkyloxy)biphenyl-4'-carbonyloxy]naphthalene-2-carboxylate.

(i)

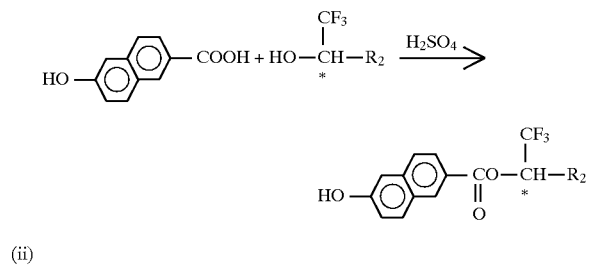

(ii)

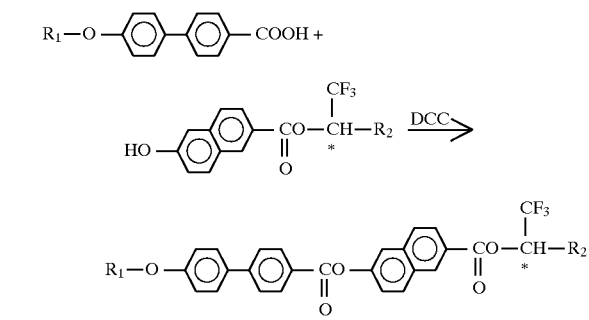

DCC: Dicyclohexylcarbodiimide (B)

(i) 2,6-Naphthalenedicarbonyl dichloride is allowed to react with optically active 1,1,1-trifluoro-2-alkanol to obtain 6-(1,1,1-trifluoro-2-alkyloxycarbonyl)naphthalene-2-carbonyl chloride.

(ii) n-Alkyl bromide is allowed to react with 4-methylcarbonyloxy-4'-hydroxybiphenyl in the presence of potassium carbonate in a solvent such as dimethylformamide and the reaction product is hydrolyzed with aqueous sodium hydroxide solution to obtain 4-n-alkyloxy-4'-hydroxybiphenyl.

(iii) The product obtained in (ii) is allowed to react with 6-(1,1,1-trifluoro-2-alkyloxy-carbonyl)naphthalene-2-carbonyl chloride to obtain 1,1,1-trifluoro-2-alkyl 6-[4-(n-alkyloxy)biphenyl4'-oxycarbonyl]naphthalene-2-carboxylate.

(i)

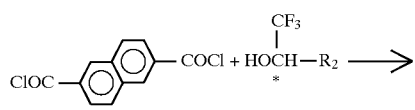

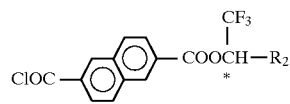

$R_3$—Br +

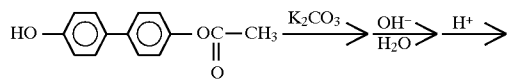

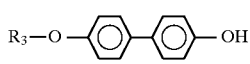

(iii)

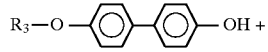

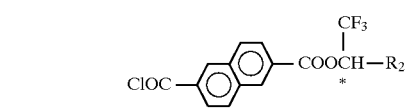

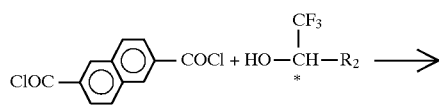

(C)

(i) 2,6-Naphthalenedicarbonyl dichloride is allowed to react with optically active 1,1,1-trifluoro-2-alkanol to obtain 6-(1,1,1-trifluoro-2-alkyloxycarbonyl)naphthalene-2-carbonyl chloride.

(ii) A fatty acid chloride is allowed to react with 4-methylcarbonyloxy-4'-hydroxybiphenyl and the reaction product is hydrolyzed with tert-butylamine to obtain 4-n-alkanoyloxy-4'-hydroxy-biphenyl.

(iii) The above product is allowed to react with 6-(1,1,1-trifluoro-2-alkyloxycarbonyl)-naphthalene-2-carboxylic acid chloride in the presence of triethylamine to obtain 1,1,1-trifluoro-2-alkyl 6-[4-(n-alkanoyloxy)biphenyl-4'-oxycarbonyl] naphthaine-2-carboxylate.

(i)

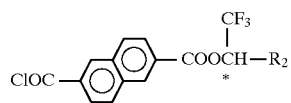

(ii)

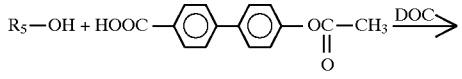

(iii)

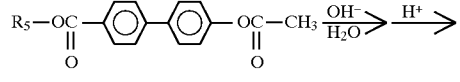

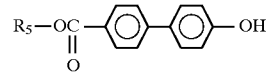

(D)

(i) 2,6-Naphthalenedicarbonyl dichloride is allowed to react with optically active 1,1,1-trifluoro-2-alkanol to obtain 6-(1,1,1-trifluoro-2-alkyloxycarbonyl)naphthalene-2-carbonyl chloride.

(ii) To a solution of n-alkyl alcohol and 4-methylcarbonyloxybiphenyl-4'-carboxylic acid in tetrahydrofuran is added dicyclohexylcarbodiimide and reaction is allowed to proceed. The reaction product is hydrolyzed with tert-butylamine to obtain 4-(n-alkyloxycarbonyl)-4'-hydroxybiphenyl.

(iii) The product is allowed to react with 6-(1,1,1-trifluoro-2-alkyloxycarbonyl)naphthalene-2-carboxylic acid chloride in the presence of triethylamine to obtain 1,1,1-trifluoro-2-alkyl 6-[4-(n-alkyloxycarbonyl)biphenyl-4'-oxycarbonyl]-naphthalene-2-carboxylate.

7
-continued (iii)

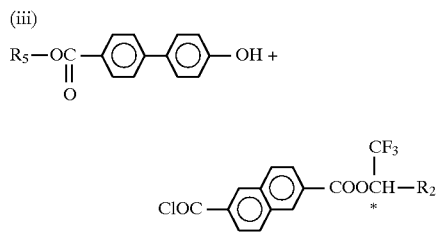

(E)

(i) 4'-Hydroxybiphenyl-4-carboxylic acid is allowed to react with alkanoyl chloride to obtain 4'-alkylcarbonyloxybiphenyl-4-carboxylic acid. The compound obtained is further allowed to react with thionyl chloride to give 4'-alkylcarbonyloxybiphenyl-4-carboxylic acid chloride.

(ii) 4'-alkylcarbonyloxybiphenyl-4-carboxylic acid chloride obtained above and 1,1,1-trifluoro-2-alkyl 6-hydroxy naphthalene-2-carboxylate obtained (A) (i) are allowed to react in methylene chloride to obtain 1,1,1-trifluoro-2-alkyl 6-(4-alkanoyloxybiphenyl-4'-carbonyloxy)naphthalene-2carboxylate.

(i)

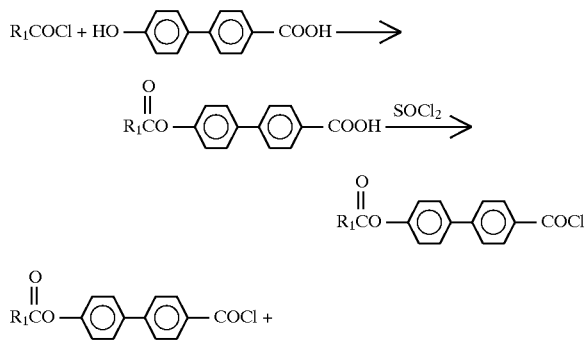

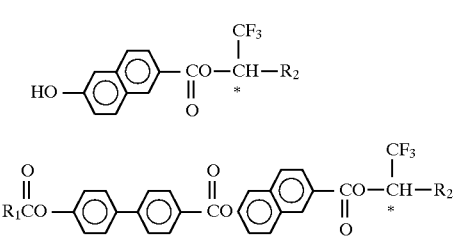

The present invention will be explained by the following examples, which should not be construed as limiting the invention.

8
EXAMPLE 1 (process A)

(1) Synthesis of 1,1,1-trifluoro-2-octyl-6-hydroxynaphthalene-2-carboxylate

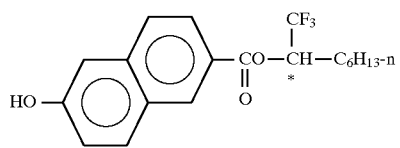

To a solution of 2-hydroxynaphthalene-6-carboxylic acid (2 g) and optically active 1,1,1-trifluoro-2-octyl alcohol (2.2 g) in ethylene chloride (50 ml) were added a few drops of concentrated sulfuric acid and the solution was refluxed with stirring for about 2 days. The reaction mixture was poured in water and the organic layer was collected. The organic layer was washed with aqueous sodium hydroxide solution and then with water and dried over anhydrous magnesium sulfate and then, the solvent was distilled off. The residue was purified by silica gel column chromatography (developer: chloroform) to obtain the titled compound (1.2 g).

(2) Synthesis of 1,1,1-trifluoro-2-octyl 6-[4-(n-octyloxy)biphenyl-4'-carbonyloxy]-naphthalene-2-carboxylate

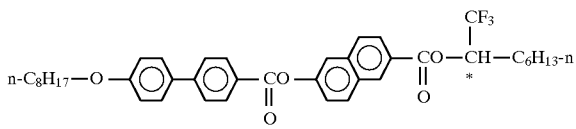

To a solution of 1-trifluoromethylheptyl 6-hydroxynaphthalene-2-carboxylate (0.6 g) obtained in (1) above and 4-n-octyloxybiphenyl-4'-carboxylic acid (0.5 g) in tetrahydrofuran (40 ml) were added dicyclohexylcarbodiimide (0.5 g) and dimethylaminopyridine (0.07 g), and the mixture was stirred for 24 hours.

After the solvent was distilled off, the residue was dissolved in dichloromethane (40 ml). The solution was washed with dilute hydrochloric acid and then with water and dried over anhydrous magnesium sulfate. The solvent was distilled off and the residue was purified by silica gel column chromatography (developer: hexane/ethyl acetate=20/1) to obtain the titled compound (0.42 g) having specific rotation $[\alpha]_D^{20}=+41.6°$.

Phase transition temperatures (°C.) which were observed under a polarizing microscope using a hot stage were as follows.

$$\text{Cry} \xleftrightarrow{93.5} S^*(3) \xleftrightarrow{147.4} S^*c \xleftrightarrow{150.7} S_A \xleftrightarrow{176.4} \text{Iso}$$

wherein S*(3): optically tristable state liquid crystal phase.

Figure 5:
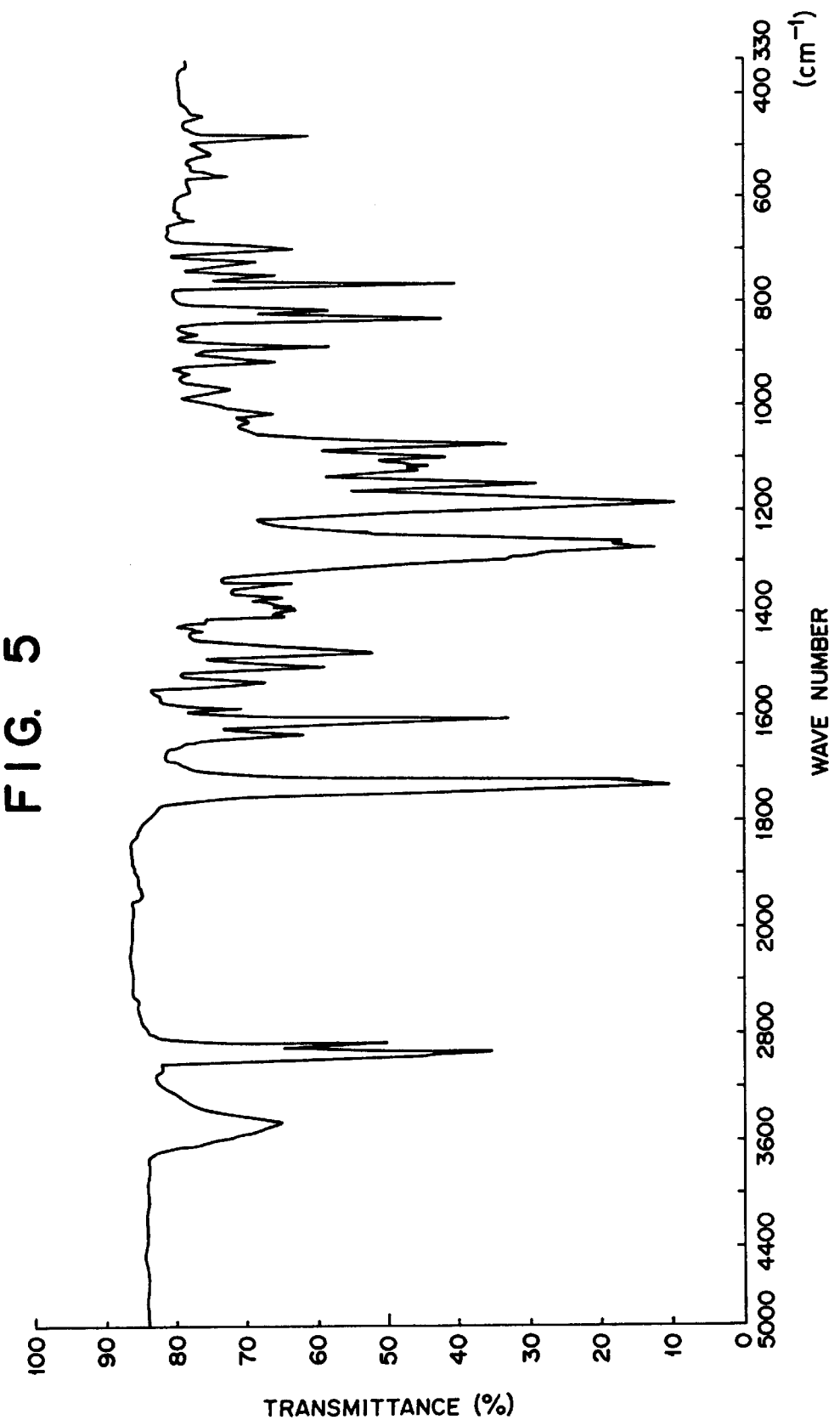
FIGS. 5–8 show IR spectra of the liquid crystal compounds of Examples 1, 2, 5 and 6.

IR spectrum (KBr) of the titled compound is shown in FIG. 5.

EXAMPLE 2 (process A)

Synthesis of 1,1,1-trifluoro-2-decyl 6-[4-(n-octyloxy) biphenyl-4'-carbonyloxy]-naphthalene-2-carboxylate

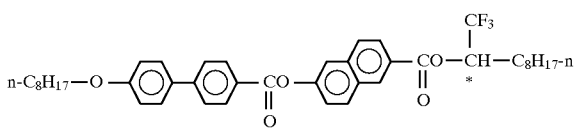

Example 1 was repeated except that optically active 1,1,1-trifluoro-2-decyl alcohol (2.3 g) was used in place of the optically active 1,1,1-trifluoro-2-octyl alcohol (2.2 g) used in (1) of Example 1 to obtain the titled compound (0.44 g) having specific rotation $[\alpha]_D^{20}=+44.2°$.

Phase transition temperatures (°C.) which were observed under a polarizing microscope using a hot stage were as follows.

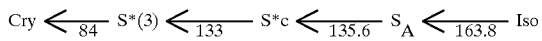

where S*(3): optically tristable state liquid crystal phase.

Figure 6:
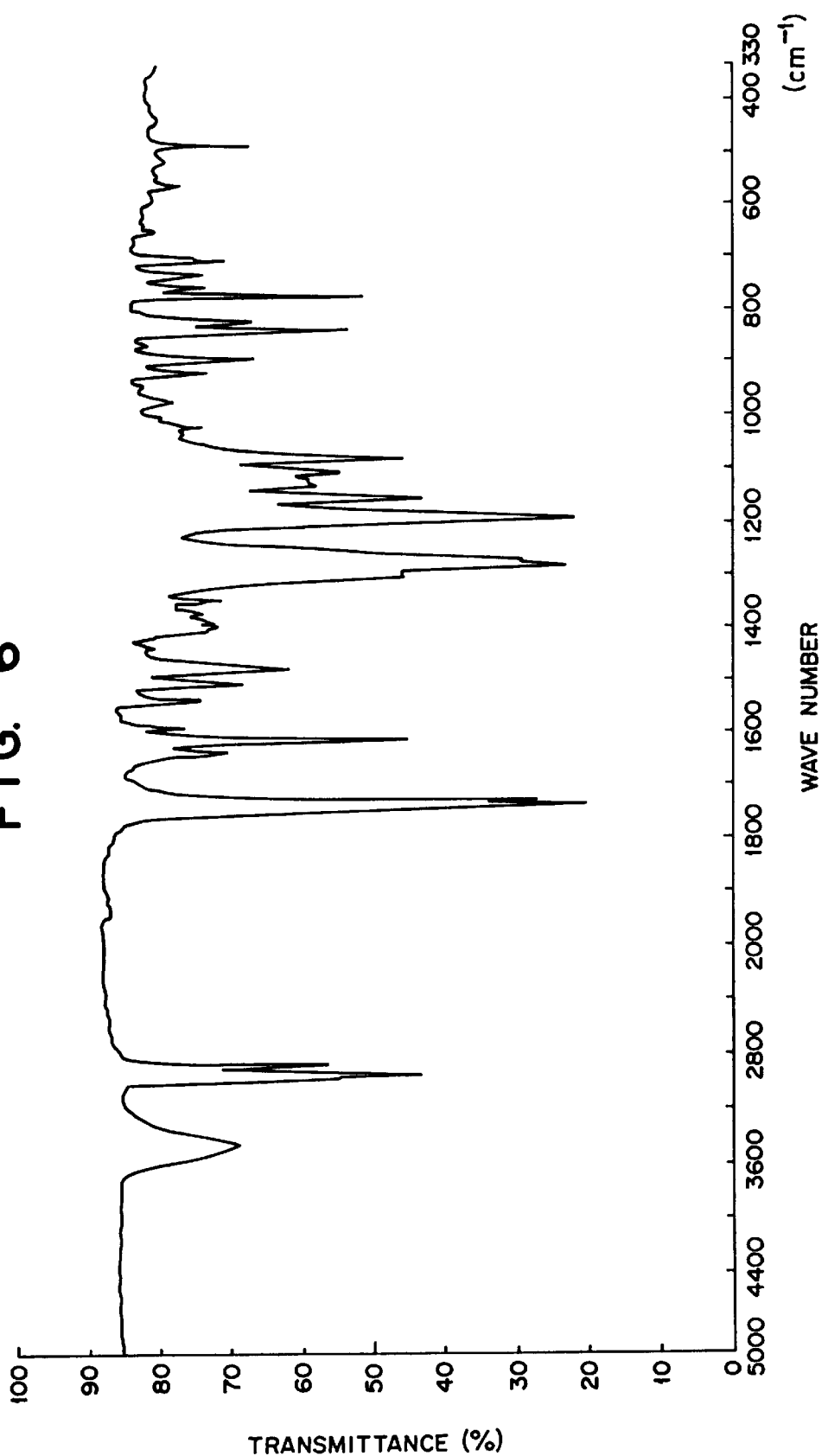

IR spectrum (KBr) of the titled compound is shown in FIG. 6.

EXAMPLE 3 (process B)

(1) Synthesis of 6-(1,1,1-trifluoro-2-octyl oxycarbonyl)naphthalene-2-carboxylic acid chloride

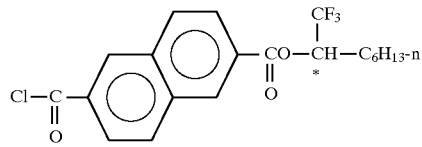

To a solution of optically active 1,1,1-trifluoro-2-octyl alcohol (1.8 g) and triethylamine (1.0 g) in methylene chloride was gradually added 2,6-naphthalenedicarbonyl dichloride (2.5 g). Furthermore, dimethylaminopyridine (0.3 g) was added and the mixture was stirred at room temperature for 24 hours. The solvent was distilled off to obtain a mixed chloride (about 2.0 g) containing the titled compound.

(2) Synthesis of 4-n-decyloxy-4'-hydroxybiphenyl

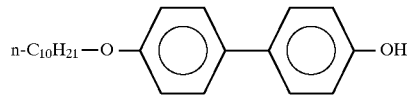

n-Decyl bromide (1.5 g) and 4-methyl-carbonyloxy-4'-hydroxybiphenyl (1.4 g) and anhydrous potassium carbonate (0.8 g) were added to dimethylformamide (50 ml).

After the mixture was stirred at 130° C. for 4 hours, the reaction mixture was poured in aqueous sodium hydroxide solution to carry out hydrolysis. The solution was made neutral with addition of dilute hydrochloric acid and was extracted with diethyl ether. After the solvent was distilled off, the residue was washed with hexane and recrystallized from water/ethanol (1/9) solution to obtain the titled compound (about 1.2 g).

(3) Synthesis of 1,1,1-trifluoro-2-octyl 6-[4-(n-decyloxy)biphenyl-4'-oxycarbonyl]-naphthalene-2-carboxylate

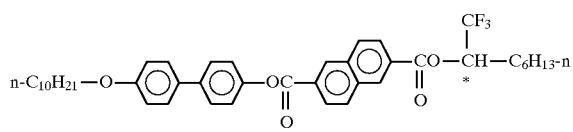

To a solution of 4-n-decyloxy-4'-hydroxy-biphenyl (0.6 g) obtained in (2) above and triethyl-amine (0.2 g) in methylene chloride (40 ml) was gradually added dropwise a solution of 6-(1,1,1-trifluoro-2-octyloxycarbonyl) naphthalene-2-carboxylic acid chloride (0.8 g) obtained in (1) above in a small amount of methylene chloride. Thereafter, dimethylaminopyridine (0.03 g) was added thereto and the mixture was stirred at room temperature for 24 hours.

The solution was made neutral with dilute hydrochloric acid and then, the methylene chloride layer was extracted and dried over anhydrous magnesium sulfate. The solvent was distilled off and the residue was purified by silica gel column chromatography (developer: hexane/ethyl acetate= 20/1) to obtain the titled compound (0.5 g). Phase transition temperatures (°C) of the titled compound which were observed under a polarizing microscope using a hot stage were as follows.

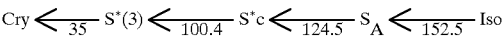

where S*(3): optically tristable state liquid crystal phase

EXAMPLE 4 (process C)

(1) Synthesis of 4-n-undecanoyloxy-4'-hydroxy-biphenyl

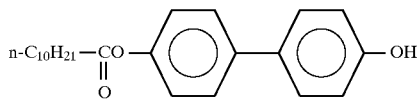

To a solution of 4-methylcarbonyloxy-4'-hydroxybiphenyl (2.3 g) and triethylamine (1.1 g) in methylene chloride (50 ml) was gradually added dropwise undecanoyl chloride (n-$C_{10}H_{21}$COCl) (2.1 g). Dimethylaminopyridine (0.3 g) was further added thereto and the mixture was stirred for 24 hours. After the solvent was distilled off, the residue was added to tetrahydrofuran containing tert-butylamine and the mixture was refluxed at 70° C. for 2 hours and hydrolyzed. After the solvent was distilled off, dilute hydrochloric acid was added to the residue to render the solution neutral and the solution was extracted with diethyl ether. After the solvent was distilled off, the residue was washed with hexane and recrystallized from water/ethanol (1/9) solution to obtain the titled compound (about 1.4 g).

(2) Synthesis of 1,1,1-trifluoro-2-octyl 6-[4-(n-undecanoyloxy)biphenyl-4'-oxycarbonyl]-naphthalene-2-carboxylate.

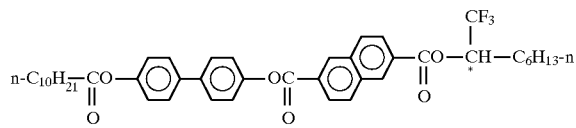

To a solution of 4-n-undecanoyloxy-4'-hydroxybiphenyl (0.6 g) obtained in (1) above and triethylamine (0.11 g) in methylene chloride (40 ml) was added gradually dropwise a solution of 6-(1,1,1-trifluoro-2-octyloxycarbonyl) naphthalene-2-carboxylic acid chloride (0.7 g) obtained in (1) of Example 3 in a small amount of methylene chloride. Thereafter, dimethylaminopyridine (0.03 g) was added thereto and the mixture was stirred at room temperature for 24 hours.

After the solution was made neutral with dilute hydrochloric acid, the methylene chloride layer was extracted and dried over anhydrous magnesium sulfate. The solvent was distilled off and the residue was purified by silica gel column chromatography (developer: hexane/ethyl acetate=20/1) to obtain the titled compound (0.44 g). Phase transition temperatures (°C) of the titled compound which were observed under a polarizing microscope using a hot stage were as follows:

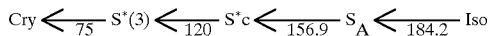

where S*(3): optically tristable state liquid crystal phase

Comparative Example 1 (process D)

(1) Synthesis of 4-n-decyloxycarbonyl-4'-hydroxybiphenyl

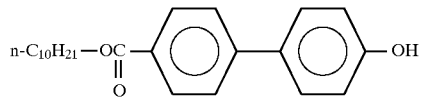

To a solution of n-decanol (1.6 g) and 4-methylcarbonyloxy-4'-carboxybiphenyl (2.6 g) in tetrahydrofuran (50 ml) were added dicyclohexylcarbodiimide (1.4 g) and dimethylaminopyridine (0.5 g), followed by stirring at room temperature for 24 hours. Thereto was added tert-butylamine and the mixture was refluxed at 70° C. for 2 hours and hydrolyzed. After the solvent was distilled off, dilute hydrochloric acid was added to make the solution neutral and the solution was extracted with diethyl ether. After the solvent was distilled off, the residue was washed with hexane and recrystallized from water/ethanol (1/9) solution to obtain the titled compound (about 2.3 g).

(2) Synthesis of 1,1,1-trifluoro-2-octyl 6-[4-(n-decyloxycarbonyl)biphenyl-4'-oxycarbonyl]-naphthalene-2-carboxylate

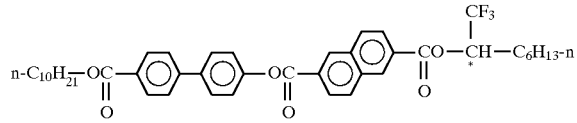

To a solution of 4-n-decyloxycarbonyl-4'-hydroxybiphenyl (0.61 g) obtained in (1) above and triethylamine (0.12 g) in methylene chloride (40 ml) was gradually added dropwise a solution of 6-(1,1,1-trifluoro-2-octyloxycarbonyl)naphthalene-2-carboxylic acid chloride (0.72 g) obtained in (1) of Example 3 in a small amount of methylene chloride. Thereafter, dimethylaminopyridine (0.03 g) was added thereto and the mixture was stirred at room temperature for 24 hours. After the solution was made neutral with dilute hydrochloric acid, the methylene chloride layer was extracted and dried over anhydrous magnesium sulfate. After the solvent was distilled off, the residue was purified by silica gel column chromatography (developer: hexane/ethyl acetate=20/1) to obtain the titled compound (0.47 g) having specific rotation $[\alpha]_D^{20}=+41.7°$.

Phase transition temperatures (°C) which were observed under a polarizing microscope using a hot state were as follows.

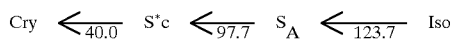

Figure 7:
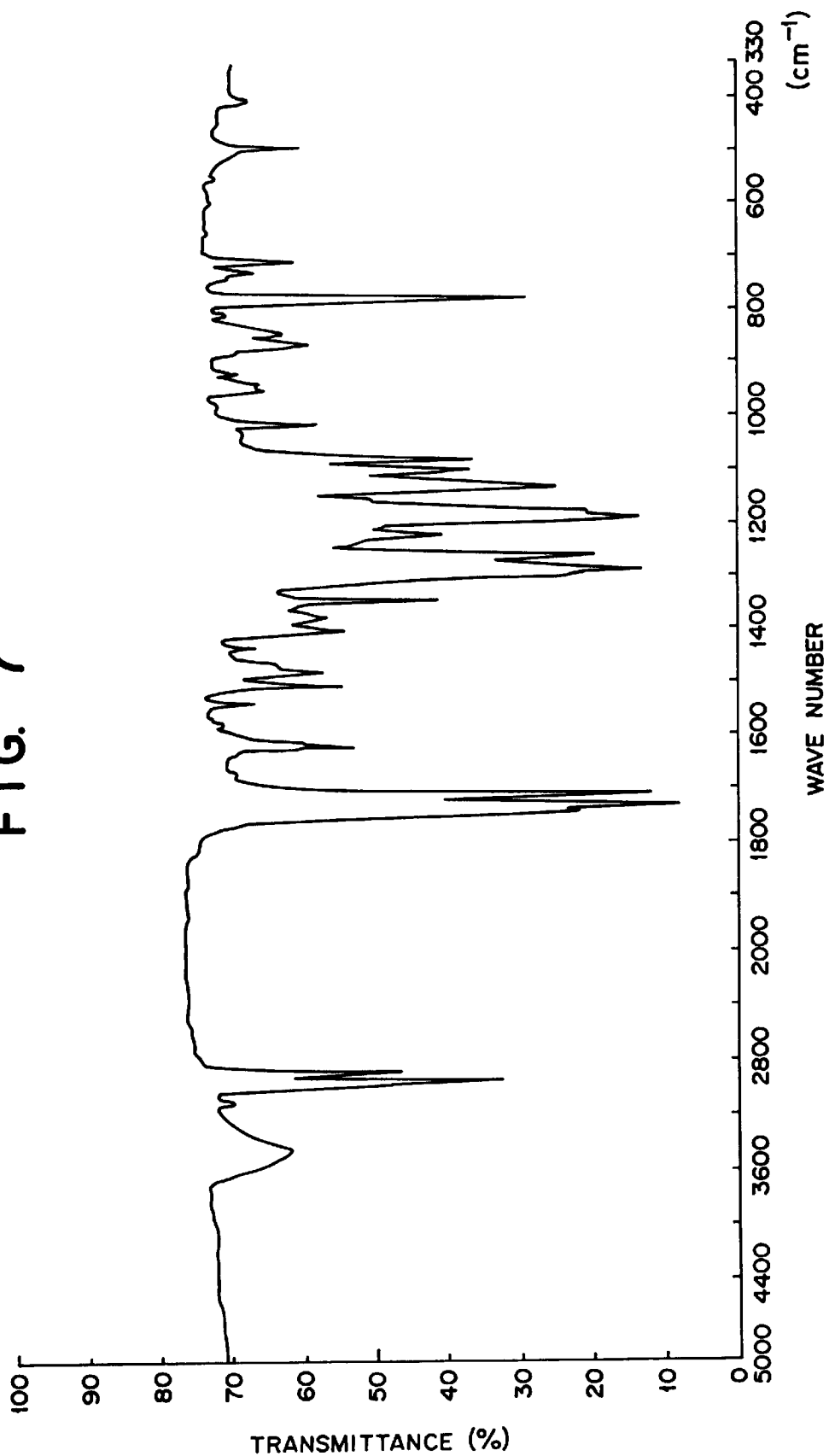

IR spectrum of the titled compound is shown in FIG. 7.

The novel liquid crystals of the present invention have bistable states and tristable states and have a wide variety of applications such as display and switching devices.

EXAMPLE 5

4'-Nonanoyloxybiphenyl-4-carboxylic acid 6-(1,1,1-trifluoro-2-octyloxycarbonyl)naphthalene-2-ester

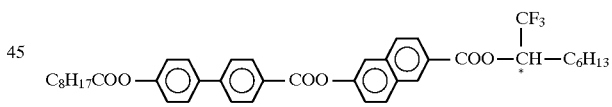

1) Synthesis of 1,1,1-trifluoro-2-octyl 6-benzyloxy-naphthalene-2-carboxylate

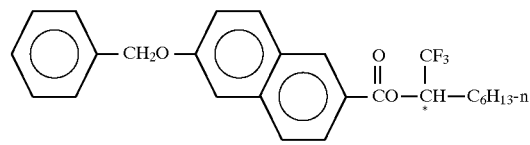

6-benzyloxy-2-naphthoic acid chloride (5.3 g) was dissolved in methylene chloride (50ml), and a solution of optically active 1,1,1-trifluoro-2-octanol (2.9 g), dimethylaminopyridine (0.6 g) and trietylamine (1.7 g) in methylene chloride (50 ml) was added to the naphthoic acid chloride solution in small portions under ice-cooling.

The reaction mixture was warmed to room temperature and allowed to react for 24 hours. The reaction solution was poured into ice-water and extracted with methylene chloride, and the methylene chloride phase was washed with dilute hydrochloric acid, water, 1N aqueous sodium carbonate solution and water in this sequence and dried over anhydrous magnesium sulfate. The solvent was removed by evaporation to give a crude product, which was purified by silica gel column chromatography (developer: toluene) and further recrystallized from ethanol to give the titled compound (3.8 g)

2) Synthesis of 1,1,1-trifluoro-2-octyl 6-hydroxynaphthalene-2-carboxylate

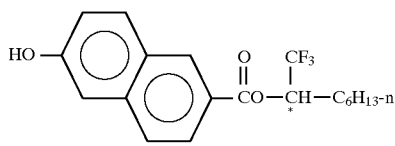

The compound obtained in 1) was dissolved in methanol (100 ml) and subjected to hydrogenolysis under a hydrogen atmosphere in the presence of 10% Pd on carbon (0.4 g) to give the titled compound (2.8 g).

3) Synthesis of 4'-n-nonanoyloxybiphenyl-4-carboxylic acid

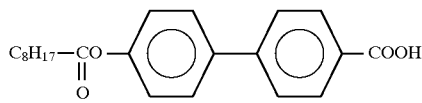

4'-Hydroxybiphenyl-4-carboxylic acid (3.5 g) and triethylamine (2.4 g) were dissolved in dichloromethane (30 ml). Nonanoyl chloride (4.3 g) and dimethylaminopyridine (0.2 g) were added to the solution, and the mixture was stirred at room temperature for about 20 hours. Dilute hydrochloric acid was added thereto, and the organic layer was separated in a separating funnel. The solvent was removed by evaportaion, and the residue was dried after washing with n-hexane to give the titled compound (5 g).

4) Synthesis of 4'-n-nonanoyloxybiphenyl-4-carboxylic acid chloride

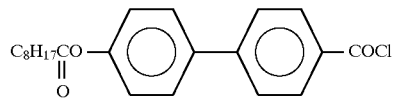

4-n-Nonanoyloxybiphenyl-4-carboxylic acid (5.0 g) was added to thionyl chloride (10 g), and N,N-dimethylformamide in a very small amount was added to the mixture. The resulting mixture was refluxed for 4 hours. The unaltered thionyl chloride was removed by evaporation to give the desired compound (5.2 g).

5) Synthesis of 4'-nonanoyloxybiphenyl-4-carboxylic acid 6-(1,1,1-trifluoro-2-octyloxycarbonyl)naphthalene-2-ester

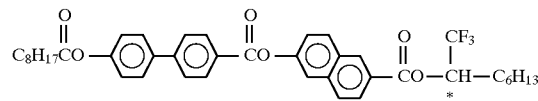

1,1,1-Trifluoro-2-octyl 6-hydroxynaphthalene-2-carboxylate (0.5 g) synthesized in 2) and triethylamine (0.16 g) were dissolved in 30 ml of methylene chloride. 4'-n-nonanoyloxybiphenyl-4-carboxylic acid chloride (0.7 g) synthesized in 4) was dissolved in methylene chloride (30 ml) and the solution was added dropwise to the aforementioned solution. Dimethylaminopyridine (0.05 g) was further added, and the mixture was stirred at room temperature for 24 hours. The reaction mixture was poured into water, and the solution was neutralized before the methylene chloride layer was separated. After the organic layer was dried over anhydrous magnesium sulfate, methylene chloride was removed by evaporation. The residue was purified by silica gel column chromatography (development solvent: hexane/ethyl acetate=20/1) to give the desired compound (0.11 g).

The phase transition temperatures (°C) observed with a microscope equipped with a hot stage were as follows:

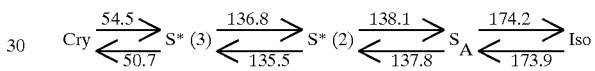

wherein S* (3) means a liquid crystal phase where the liquid crystal shows optically tristable states.

Figure 8:
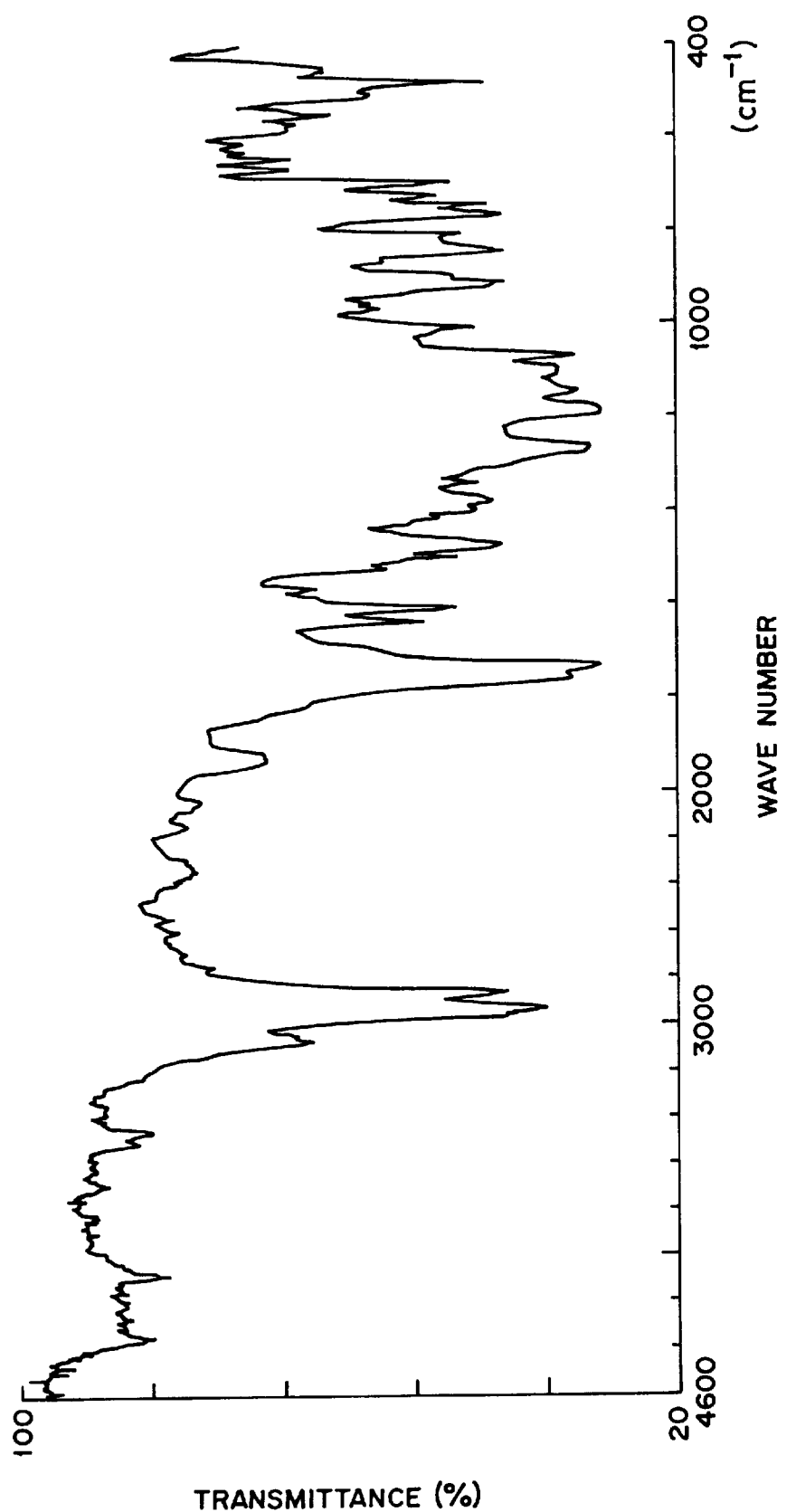

The infrared spectrum of the titled compound is shown in FIG. 8.

EXAMPLE 6

6-(1,1,1-Trifluoro-2-octyloxycarbonyl) naphthalene-2-carboxylic acid 4'-nonanoyloxybiphenyl-4-ester

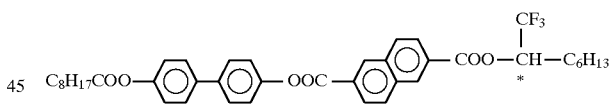

1) Synthesis of 4-n-Nonanoyloxy-4'-hydroxybiphenyl

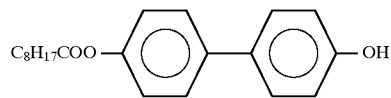

4,4'-Diphenol (0.1 g) and triethylamine (0.57 g) were dissolved in dichloromethane (20 ml). Nonanoyl chloride (1.0 g) and dimethylpyridine (0.2 g) were added thereto, and the mixture was stirred at room temperature for about 20 hours. The reaction mixture was poured into ice-water and subjected to extraction with dichloromethane. The organic layer was dried over anhydrous magnesium sulfate and removed by evaporation to give a crude product. It was purified by silica gel column chromatography (developer: hexane/ethyl acetate=3/2) to give the titled compound (0.28 g).

2) Synthesis of 2,6-Naphthalenedicarboxylic acid dichloride

2,6-Naphthalenedicarboxylic acid (0.5 g) was added to 10 ml of thionyl chloride, and N,N-dimethylformamide in a very small amount was added to the mixture. The resulting mixture was refluxed for 4 hours. The unaltered thionyl chloride was removed by evaporation to give the desired compound (0.48 g).

3) Synthesis of 6-(1,1,1-trifluoro-2-octyloxycarbonyl)-naphthalene-2-carboxylic acid 4'-nonanoyloxybiphenyl-4-ester

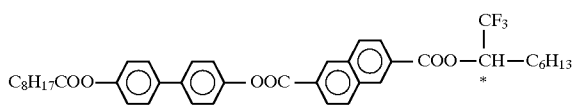

A solution of 2,6-naphthalenedicarboxylic acid dichloride (0.48 g) obtained in 2) in methylene chloride (20 ml) was added in small portions to a solution of optically active 1,1,1-trifluoro-2-octanol (0.16 g), dimethylaminopyridine (0.06 g) and triethylamine (0.18 g) in methylene chloride (20 ml) under ice-cooling. After the mixture was stirred for about 20 hours, 4-n-nonanoyloxy-4'-hydroxybiphenyl (0.28 g) obtained in 1) dissolved in methylene chloride (20 ml) was added to the mixture in small portions, and the mixture was stirred for about 20 hours. The reaction mixture was then poured into ice-water and extracted with methylene chloride. The methylene chloride layer was washed with dilute hydrochlorice acid, water, 1N aqueous sodium carbonate solution and water in this sequence and dried over anhydrous magnesium sulfate. The solvent was removed by evaporation to give a crude product, which was purified by silica gel column chromatography (development solvent: hexane/ethyl acetate=10/1) to give 0.1 g of the titled compound.

Phase transition temperature (°C) which were observed under a polarizing microscope equipped with a hot stage were as follows:

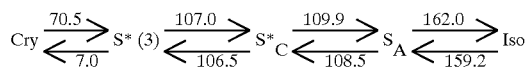

wherein S* (3) means an optically tristable state liquid crystal phase.

Comparative Example 2

4'-(n-Octyloxycarbonyl)biphenyl-4-carboxylic acid 6-(1,1,1-trifluoro-2-octyloxycarbonyl)naphthalene-2-ester

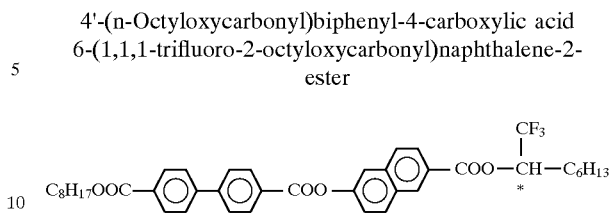

1) Synthesis of 4,4'-biphenyldicarboxylic acid dichloride

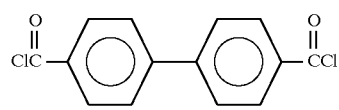

4,4'-Biphenyldicarboxylic acid (1.1 g) was added to thionyl chloride (15 ml). N,N-Dimethylformamide in a very small amount was added thereto, and the mixture was heated under reflux for 4 hours. Unaltered thionyl chloride was removed by evaporation to give the titled compound (1.2 g).

2) Synthesis of 4'-(n-octyloxycarbonyl)biphenyl-4-carboxylic acid 6-(1,1,1-trifluoro-2-octyloxycarbonyl)-naphthalene-2-ester

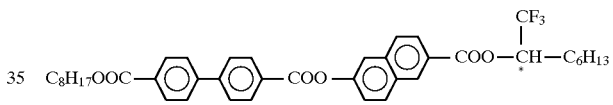

To a solution of 1,1,1-trifluoro-2-octyl 6-hydroxynaphthalene-2-carboxylate (1.2 g) obtained in the step 2) in Example 6, dimethylaminopyridine (0.03 g) and triethylamine (0.44 g) in methylene chloride (20 ml) was added a solution of 4,4'-biphenyldicarboxylic acid chloride (1.2 g) in methylene chloride (30 ml) in small portions under ice-cooling, and the mixture was stirred for about 20 hours. Then, octanol (0.3 g) was added in small portions to the reaction mixture, and the mixture was further stirred for 20 hours. The reaction mixture was poured into ice-water and subjected to extraction with methylene chloride. The methylene chloride layer was washed with dilute hydrochloric acid, water, 1N aqueous sodium hydrogen carbonate solution and water in this sequence and dried over anhydrous magnesium sulfate. The solvent was removed by evaporation to give a crude product, which was purified by silica gel column chromatography (development solvent: hexane/ethyl acetate=10/0.5) to give the titled compound (0.2 g).

Phase transition temperatures (°C) observed under a polarizing microscope equipped with a hot stage were as follows:

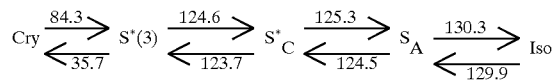

wherein S* (3) means an optically tristable state liquid crystal phase.

Comparative Example 3

6-(1,1,1-Trifluoro-2-octyloxycarbonyl)-naphthalene-2-carboxylic acid 4'-(n-octyloxycarbonyl)biphenyl-4-ester

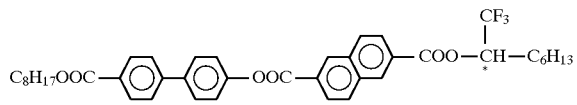

1) Synthesis of 4-n-octyloxycarbonyl-4'-hydroxybiphenyl

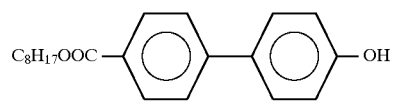

4'-Benzyloxybiphenyl-4-carboxylic acid chloride (3.4 g) was dissolved in methylene chloride (50 ml) and added in small portions to a solution of octanol (1.2 g), dimethylaminopyridine (0.35 g) and triethylamine (1.0 g) in methylene chloride (30 ml) under ice-cooling. After the reaction mixture was stirred for about 20 hours, it was poured into ice-water and extracted with methylene chloride. The solvent was removed by evaporation to give a crude product, which was then purified by silica gel column chromatography (development solvent: hexane/ethyl acetate=10/0.5) to give octyl 4'-benzyloxybiphenyl- 4-carboxylate (0.7 g).

The compound was dissolved in ethanol (30 ml). After stirring for about 20 hours under hydrogen atmosphere in the presence of 0.15 g of Pd-carbon, the catalyst was removed by filtration, and ethanol was removed by evaporation to give the titled compound (0.55 g).

2) 6-( 1,1,1-trifluoro-2-octyloxycarbonyl) naphthalene-2-carboxylic acid 4'-(n-octyloxycarbonyl)biphenyl-4-ester

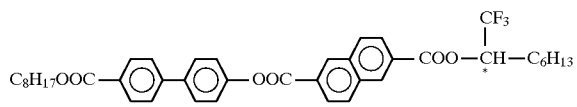

Optically active 1,1,1-trifluoro-2-octanol (0.3 g), dimethylformamide (0.2 g) and triethylamine (0.18 g) were dissolved in methylene chloride (20 ml). To this solution was added in small portions a solution of 2,6-naphthalenedicarboxylic acid dichloride (0.8 g) obtained in the step 2) of Example 7 in methylene chloride (50 ml) under ice-cooling, and the mixture was stirred for about 20 hours. Next, 4-n-octyloxycarbonyl-4'-hydroxybiphenyl (0.55 g) obtained in the step 1) was dissolved in methylene chloride (30 ml) and added in small portions to the reaction mixture. The resulting mixture was stirred for about 20 hours.

The reaction mixture was poured into ice-water and extracted with methylene chloride. The methylene chloride layer was washed with dilute hydrochloric acid, water, 1N aqueous sodium hydrogen carbonate solution and water in this sequence and dried over anhydrous magnesium sulfate. The solvent was removed by evaporation to give a crude product. Silica gel column chromatography treatment (development solvent: hexane/ethyl acetate=10/0.5) of the crude product gave 0.1 g of the titled compound.

Phase transition temperatures(°C) which were observed under a polarizing microscope equipped with a hot stage were as follows:

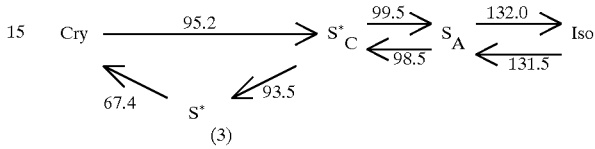

wherein $S^*$ (3) means an optically tristable state liquid crystal phase.

EXAMPLE 7

Hysteresis curves of the compounds obtained in Examples 5–6 and Comparative 2–3 were measured with the following apparatuses:

A polarizing optical microscope OLYMPUS model BHSP)

A photo metor (SANKEI SPS-5A)

A photo cell (Hamamatsu R-636)

A high speed power Amplifier (NF 4005)

A digitizing osilloscope (YHP HP 54501A)

A function generator (YHP HP 3314A)

A hot stage (Metler FP 82)

A central processor (Metler FP 80)

Sample preparation

Sample cells were constructed from two grass substrates with patterned ITO (indium-tin-oxide). The substrates were initially spin-coated with the polyimides (LX500 produced by Hitachi Kasei Ltd.) and were then rubbed with nylon cloths on a rotating cylinder under several kinds of rubbing conditions. The sample cells were composed of two substrates thus processed, the rubbing directions of which were mutually parallel. The cell spacing was 1.6 μm. After the cell was filled with antiferroelectric liquid crystal by capillary suction in the isotropic phase, it was cooled slowly (-0.1~-1° C./min) to the $S^*$ (3) phase.

Evaluation of samples

Figure 10:
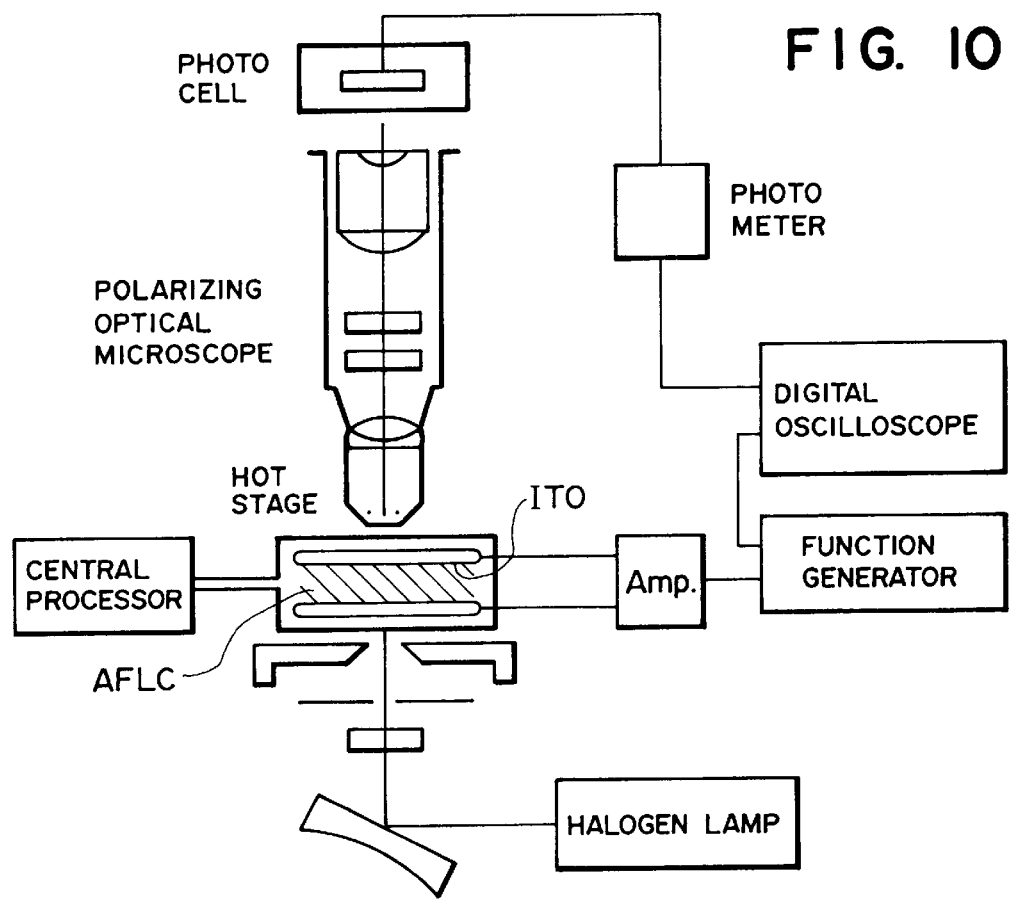
FIG. 10 is a polarizing microscope with a hot stage used for hysteresis measurement.

The orientation of the sample was observed under a polarizing microscope. In order to control the sample temperature, a hot stage (Mettler FP 82) and a central processor (Mettler FP 80) were used. The electrooptical properties were evaluated by the measurement system, as shown in FIG. 10. The light transmitted through the sample cell was detected by a photo cell. Pulses were synthesized in a function generator and were supplied to the sample cells through a bipolar amplifier.

A liquid crystal cell having a rubbed polyimide oriented film on the ITO electrode substrate late and a thickness of 1.6 μm was filled with the liquid crystal compound obtained in Example 5, i.e., 4'-nonanoyloxybiphenyl-4-carboxylic acid 6-(1,1,1-trifluoro-2-octyloxycarbonyl)naphthalene-2-ester, in an isotrolpic phase, to make a liquid crystal thin film cell.

The liquid crystal cell thus prepared was arranged on a polarizing microscope equipped with a photomulitplier which was made of two polarizing plates orthogonalized to each other so that darkness is realized at a voltage of 0 V.

Figure 9A:
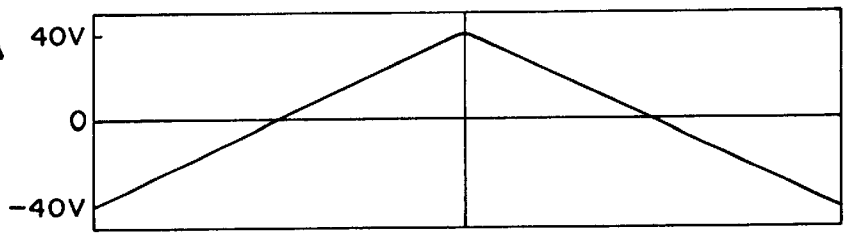
Figure 9B:
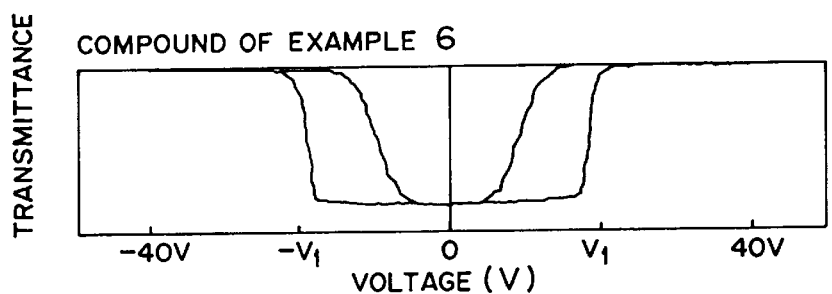

The liquid crystal cell was slowly cooled down to the $S_A$ phase at a temperature gradient in the range of 0.1–1.0° C./min. The liquid crystal cell was further cooled down, and a triangular wave voltage of ±40 V and 1 Hz as shown in FIG. 9A was applied at the temperature range of 135.5°–50.7° C. On account of the applied voltage and the transmittance effect at a temperature of 115° C., a hysteresis curve was obtained as shown in FIG. 9B. In the switching process from 0 to $+V_1$, the liquid crystal cell displays the dark state. The transmittance steeply increases at $+V_1$ and the cell exhibits the light state. In the switching process from +40V to $+V_3$, the liquid crystal cell displays the light state and steeply changes into the dark state at $+V_3$. The liquid crystal cell displays the dark state during the switching process from 0V to $-V_1$ and turns into the light state after the steep increase of the transmittance at $-V_1$. In the switching process −40V to $V_3$, the liquid crystal cell displays the light state and steeply turns into the dark state at −V3. It was observed that the liquid crystal cell follows the three optical states from light to dark and from dark to light with switching when the applied voltage varies within the range of +40 V to −40 V. It was thus confirmed that the liquid crystal cell possesses three stable orientation states.

Figure 9C:
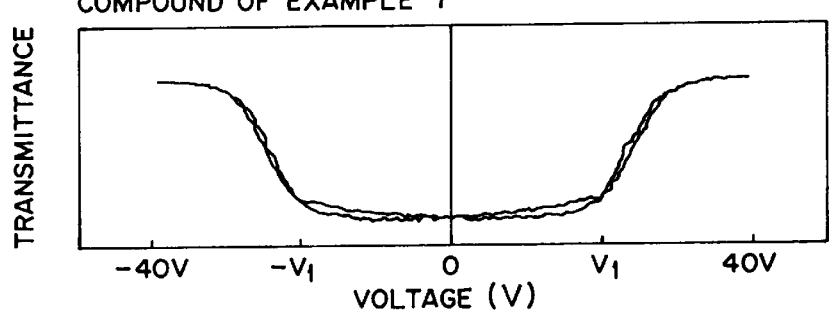
Figure 9D:
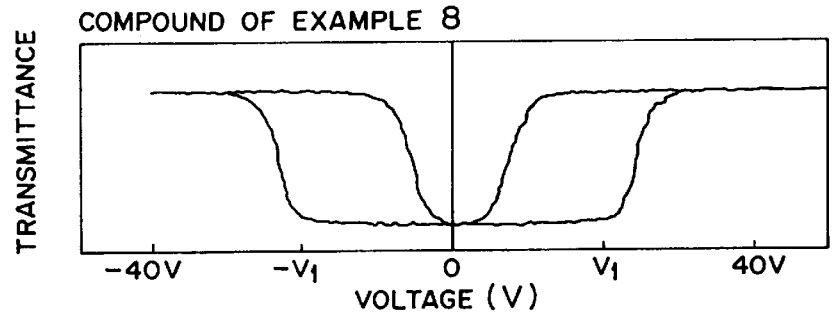
Figure 9E:
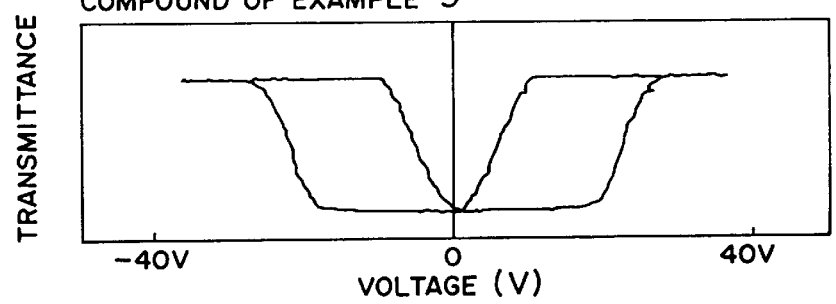

Hysteresis curves shown in FIGS. 9C–9E were obtained for the liquid crystal compounds obtained in the Example 6 Comparative Examples 2–3, by the same manner as above.

The liquid crystal compounds obtained in the Example 5, and Comparative Examples 2–3 exhibited distinctive hysteresis.

EXAMPLE 8

Memory margin was measured for the compounds obtained in the Examples 5–6 and Comparative Examples 2–3. Memory margin was calculated from the hysteresis curves.

Figure 11:
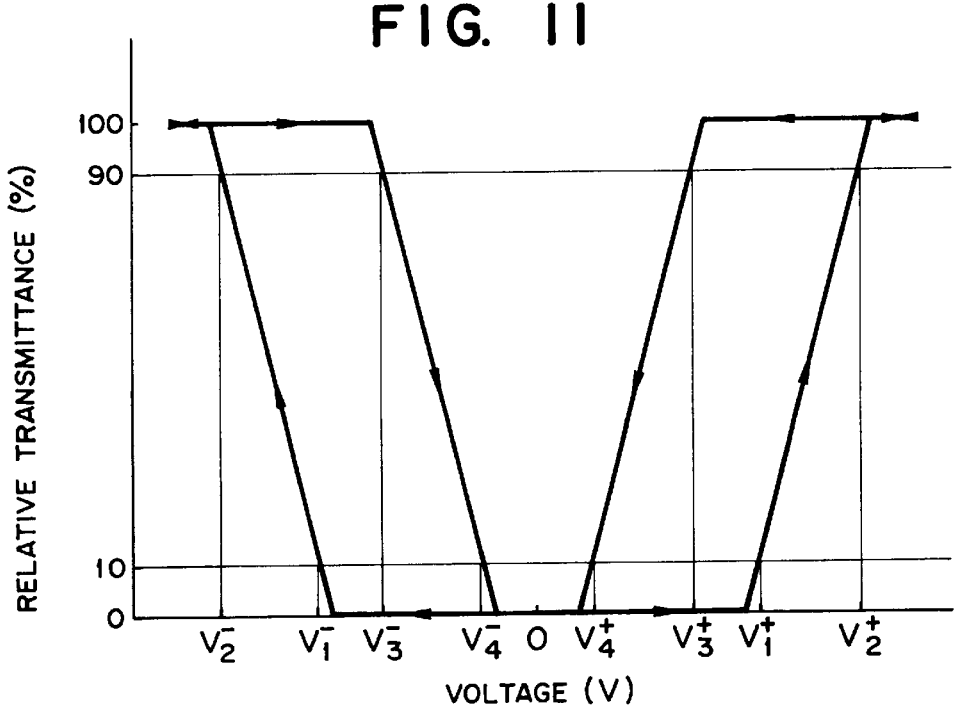
FIG. 11 is a figure for calculating the memory margin.

Hysteresis curves were obtained by the method described in the Example 7. In FIG. 11, the relative light transmittance is represented by 0% at the voltage of 0 V and 100% at the voltage where the maximum transmittance is obtained. The voltage corresponding to the relative transmittance 10% starting from 0 V is represented by $V_1^+$, and the voltage needed for the relative transmittance of 90% is represented by $V_2^+$. When the relative transmittance varies from 100% to 90%, the corresponding voltage is represented by $V_3^+$. When the relative transmittance reaches 10%, the voltage is represented by $V_4^+$, $V_1^-$, $V_2^-$, $V_3^-$ and $V_4^-$ are defined similarly. Memory margin is calculated from the following equation:

$$M = \frac{V_1^+ - V_3^+}{V_2^+ - V_1^+} = \frac{V_1^- - V_3^-}{V_2^- - V_1^-}$$

The results are shown in Table 1.

TABLE 1

|  | Memory Margin (M) | T–$T_{CA}$ (°C.) |
| --- | --- | --- |
| Compound of Example 5 | 1.84 | −20 |
| Compound of Example 6 | <0 | −20 |
| Comparative Example 2 | 2.34 | −20 |
| Comparative Example 3 | 1.60 | −20 |

Memory margin is preferably in the range of 1.5 or more.

EXAMPLE 9

Response times of the compounds obtained in Examples 5–6 and Comparative Examples 2–3 were measured when an electric voltage was applied. The results were showing in Table 2. A liquid crystal cell was prepared in the same manner as in Example 7, and a pulse voltage in place of a triangular wave voltage was applied to the cell. The response time τ(r) for the transition from the first stable state (dark state)to the second stable state (light state), the response time τ(d) for the transition from the second stable state (light state) to the first stable state (dark state), and the response time τ for the transition from the second stable state (light state) to the third stable state (light state) through the first stable state were measured. Smaller response times τ(r), τ(d) and τ, to electric field means more rapid response and desirable. The response times of the compounds in Examples 6–9 were compared with each other at a temperature which is 10° C. lower than the temperature for the transitions from SA or $S^*_C$ to $S^*(3)$.

TABLE 2

| Example | τ(r) μsec | τ(d) μsec | τ μsec |
| --- | --- | --- | --- |
| 3 | 1.2 | 45.2 | 1.8 |
| 6 | 1.5 | 138.0 | 2.4 |
| Comparative Example 2 | 5.2 | 35.2 | 2.9 |
| Comparative Example 3 | 14.8 | 228.0 | 8.2 |

As for τ(r), the compound of Example 6 has a response time in a proportion of 1.25 times, 4.3 times and 12.3 times shorter than the compounds of Examples 6 Comparative 2 and 3, respectively.

As for τ(d), the compound of Example 5 has a response time in a proportion of 3 times and 5 times shorter than the compounds of Examples 6 Comparative Example 3 respectively.

As for τ, the compound of Example 5 has a response time in a proportion of 1.3 times, 1.6 times and 4.5 times shorter than the compounds of Example 6 Comparative Examples 2 and 3 respectively.

Among the compounds in Examples 5–6 and Comparative Examples 2–3, the compound in Example 5 is the most preferable.

We claim:

1. A liquid crystal compound which is represented by the formula [I]:

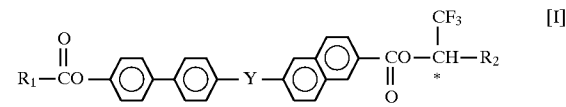

wherein $R_1$ represents an alkyl group of 5–18 carbon atoms; $R_2$ represents an alkyl group of 6–16 carbon atoms; Y represents

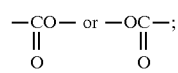

and * indicates an optically active center, and which exhibits optically tristable states in S*(3) phase.

2. A liquid crystal compound according to claim 1 wherein Y represents

3. A liquid crystal compound according to claim 1 wherein $R_1$ represents an alkyl group having 8 carbon atoms.

4. A liquid crystal compound according to claim 1 wherein $R_2$ represents an alkyl group having 6 carbon atoms.

5. A liquid crystal compound according to claim 1 wherein $R_1$ represents an alkyl group having 10 carbon atoms.

6. A liquid crystal compound according to claim 2 wherein $R_1$ represents an alkyl group having 8 carbon atoms.

7. A liquid crystal compound according to claim 2 wherein $R_2$ represents an alkyl group having 6 carbon atoms.

8. A liquid crystal compound according to claim 2 wherein $R_1$ represents an alkyl group having 8 carbon atoms and $R_2$ represents an alkyl group having 6 carbon atoms.

* * * * *